United States Patent [19]

Fairbanks

[11] 4,233,965
[45] Nov. 18, 1980

[54] METHOD AND APPARATUS FOR THE THERAPEUTIC TREATMENT OF LIVING TISSUE

[75] Inventor: Everitt E. Fairbanks, Arleta, Calif.

[73] Assignee: CAS Products, Inc., Los Angeles, Calif.

[21] Appl. No.: 869,624

[22] Filed: Jan. 16, 1978

[51] Int. Cl.³ .............................................. A61N 1/42
[52] U.S. Cl. ................................. 128/1.5; 128/420 R; 128/421
[58] Field of Search ..................... 128/1.3, 1.5, 419 F, 128/419 R, 420 R, 421, 422, 423 R, 424

[56] References Cited

U.S. PATENT DOCUMENTS

| | | | |
|---|---|---|---|
| 96,004 | 10/1869 | Smith | 128/421 |
| 3,055,372 | 9/1962 | Browner | 128/421 |
| 3,476,117 | 11/1969 | Jonsson | 128/421 |
| 3,645,267 | 2/1972 | Hagfors | 128/421 |
| 3,726,285 | 4/1973 | Bowers et al. | 128/422 |
| 3,769,985 | 11/1973 | Fujii et al. | 128/419 R |
| 3,773,051 | 11/1973 | Holcomb et al. | 128/422 |
| 3,794,022 | 2/1974 | Nawracaj et al. | 128/422 |
| 3,841,305 | 10/1974 | Hallgren | 128/419 R |
| 3,881,494 | 5/1975 | Paul, Jr. | 128/421 |
| 3,888,261 | 6/1975 | Maurer | 128/421 |
| 3,893,462 | 7/1975 | Manning | 128/421 |
| 3,902,502 | 9/1975 | Liss | 128/422 |
| 3,911,930 | 10/1975 | Hagfers et al. | 128/421 |
| 3,915,151 | 10/1975 | Kraus | 128/419 F |
| 3,918,459 | 11/1975 | Horn | 128/419 R |
| 3,924,641 | 12/1975 | Weiss | 128/421 |
| 3,989,051 | 11/1976 | Nozhnikov et al. | 128/421 |
| 4,019,510 | 4/1977 | Ellis | 128/421 |
| 4,019,519 | 4/1977 | Geerling | 128/422 |
| 4,105,017 | 8/1978 | Ryaby et al. | 128/419 F |

FOREIGN PATENT DOCUMENTS

| | | | |
|---|---|---|---|
| 497021 | 1/1975 | U.S.S.R. | 178/419 F |

*Primary Examiner*—William E. Kamm
*Attorney, Agent, or Firm*—Lyon & Lyon

[57] ABSTRACT

Disclosed herein is a method and device for the therapeutic treatment of living tissue to assist in the healing of biological traumas and providing treatment of conditions such as arthritis. Positive square wave current pulses are applied between two electrodes positioned on the skin of the patient, one of the electrodes being provided with a concentric electromagnet to produce a magnetic field which forces the applied current into the tissues being treated.

27 Claims, 11 Drawing Figures

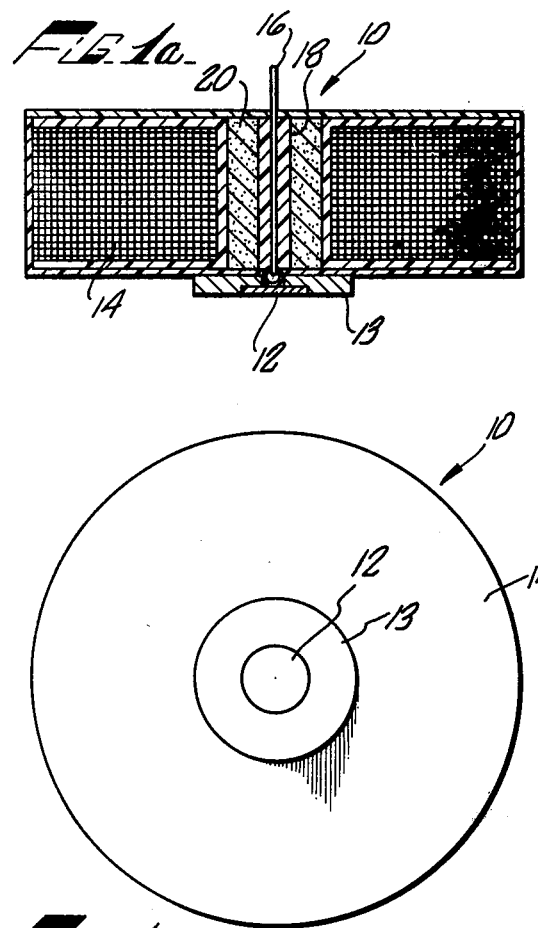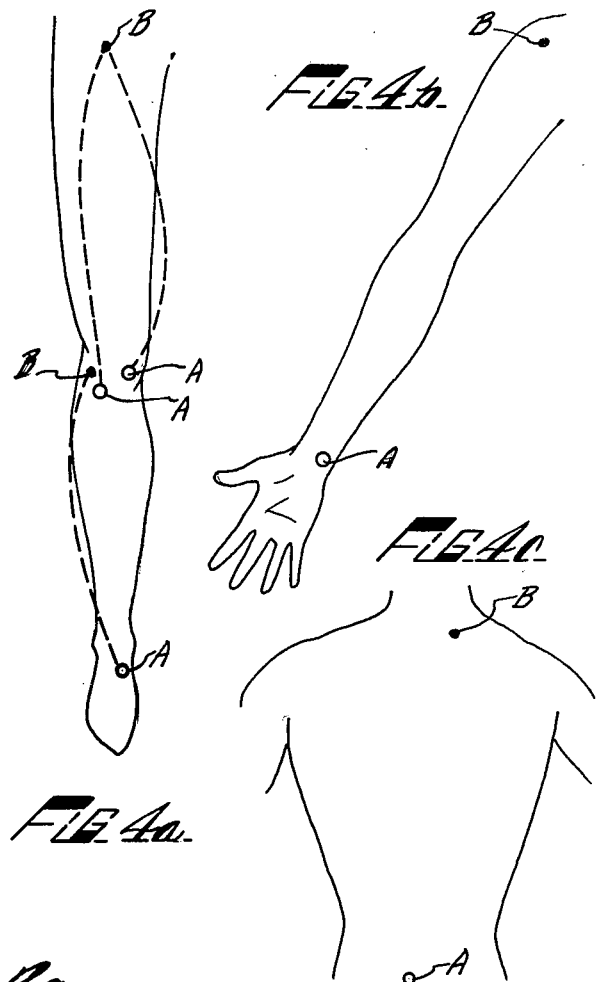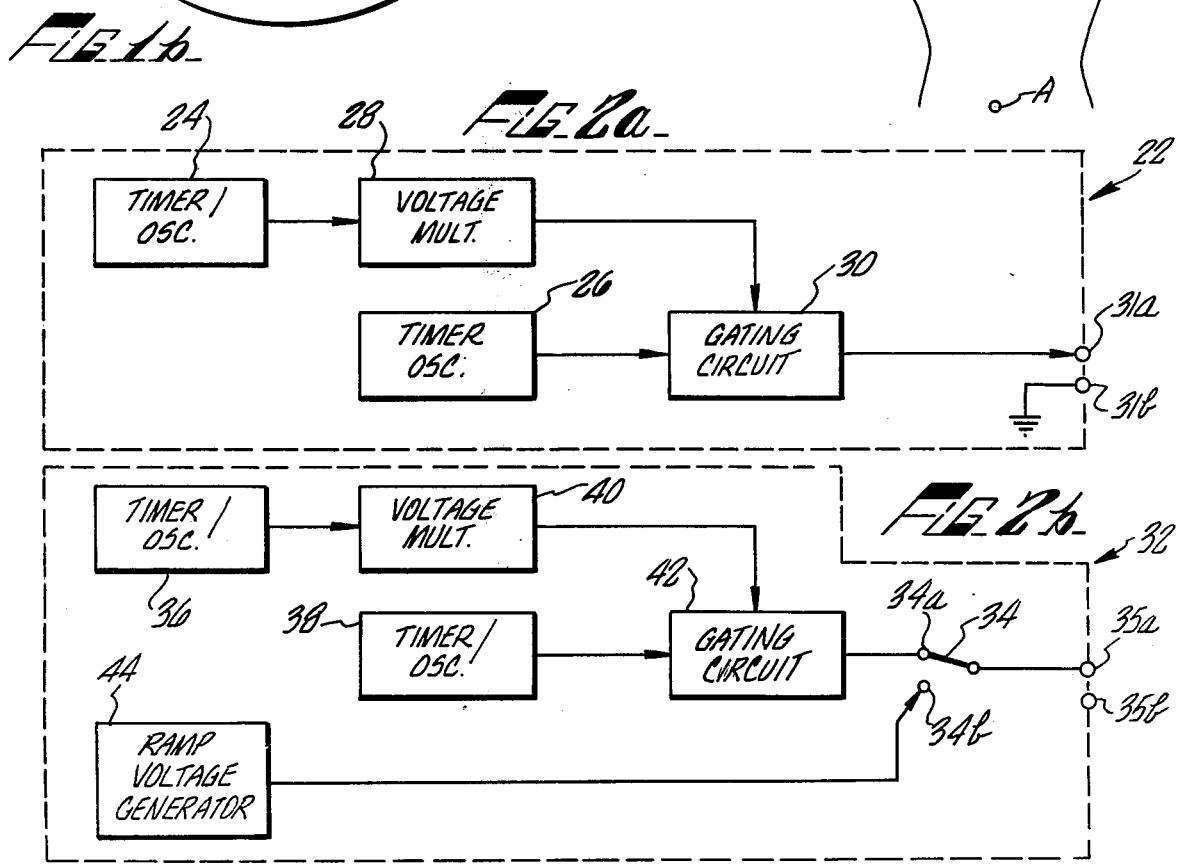

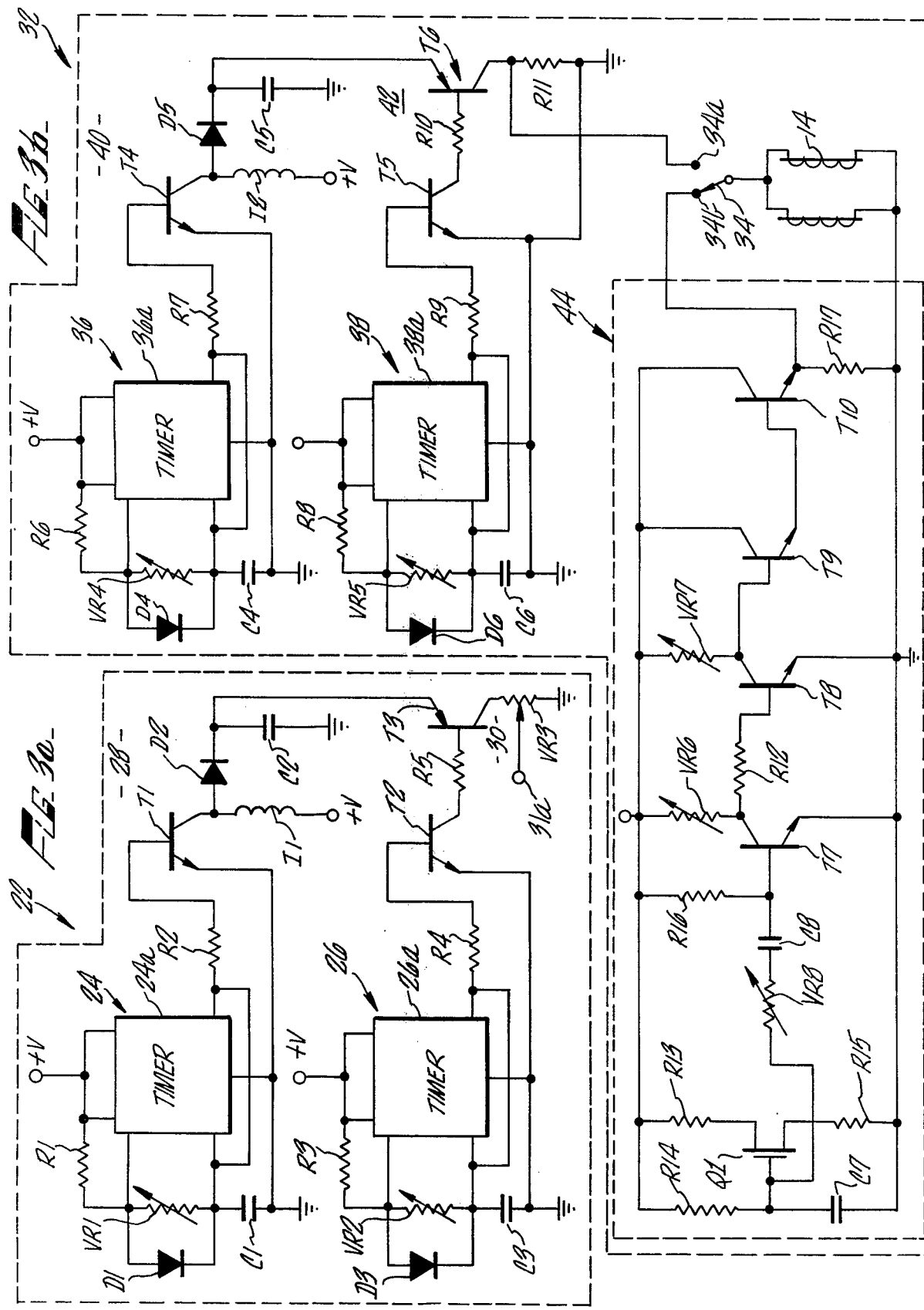

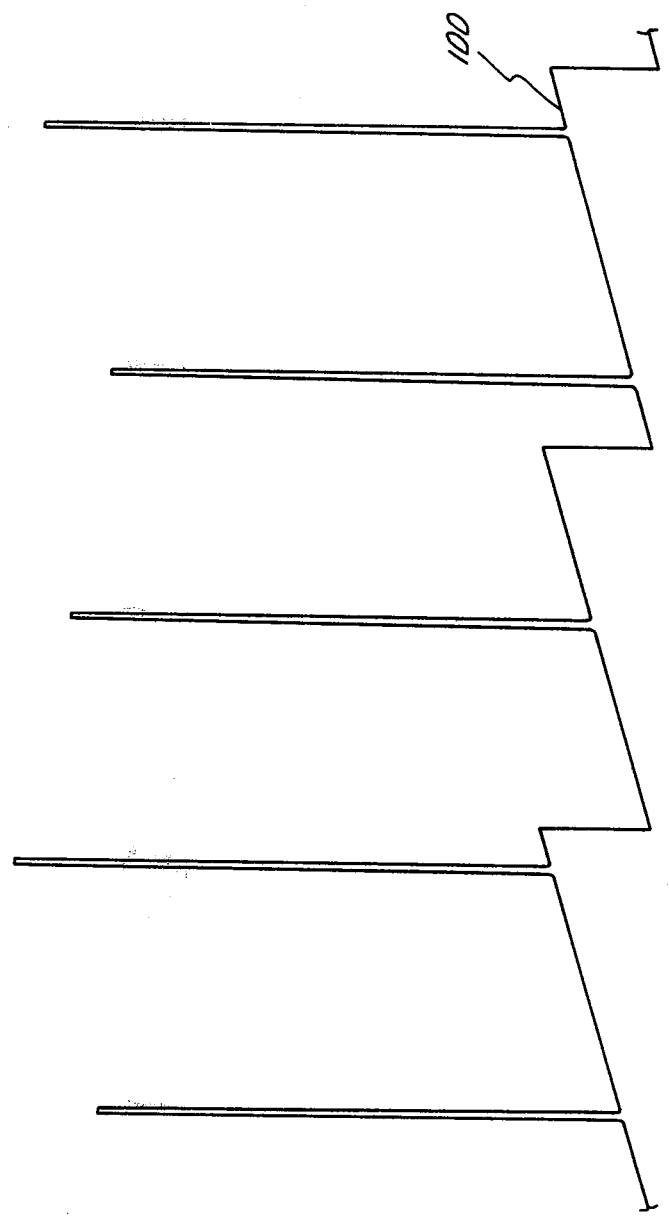

METHOD AND APPARATUS FOR THE THERAPEUTIC TREATMENT OF LIVING TISSUE

BACKGROUND OF THE INVENTION

The present invention relates to methods and devices for electrical stimulation of biological functions to assist in the treatment of certain abnormal biological conditions.

Human cells contain a bioelectrical potential across the cell membrane, thought to be generated by the differing concentrations of sodium and potassium ions inside and outside the cell. Under equilibrium conditions the electrical currents caused by the movement of sodium and potassium ions through the semipermeable cell membrane are equal, resulting in a zero net current flow and a resting potential difference of approximately −90 millivolts (mV). When the cell is electrically stimulated either by a nerve signal or by an external stimulus, the cell passes through a "cell action potential cycle." The sodium ionic current into the cell increases until the cell's internal voltage reaches a threshold level of approximately −60 mV, at which point the cell potential increases without further stimulation to a peak of approximately +20 mV. The cell is then referred to as being in a "depolarized" state. The cell then "repolarizes" to a −90 mV state as the ionic concentrations return to equilibrium. This cell activity has been referred to as the "sodium-potassium pump," as generally described for example at pages 7–21 of *Biophysical Measurements*, by Peter Strong, published by Tektronix, Inc. (1971).

The sodium-potassium pump action is thought to be important in the maintenance of physical health, and is normally provided by ordinary nerve signals in healthy tissue. When ordinary nerve signals are interrupted, however, as for example by trauma or by calcification in the case of arthritis, it is believed that this cell action may be reduced or impaired or may cease altogether. Application of external voltage pulses is thought to assist in reestablishing cell action within the affected area and thus promote healing.

Devices for applying electrical stimulation to the human body are well known in the art, but they have generally utilized alternating electrical fields because of the possibility of undesired electrolysis at the point of contact between the tissue and the electrodes. Further, such devices generally have not utilized magnetic fields to aid the penetration of the electric current into the tissues being treated. As a result it is believed that the electric current failed to penetrate deeply into the tissue, but rather traveled along the skin from one electrode to the other. Healing of deep tissue therefore was not significantly aided. Current levels sufficient to penetrate deep tissue were often hazardous to the patient.

In U.S. Pat. No. 3,915,151 (Kraus), there was disclosed a device for treating injured body tissue by passing alternating electric and magnetic fields through the tissue at the same time, and two fields having approximately the same energy content and being approximately ninety degrees out of phase. However, there was no direct connection between the electrodes and the patient, and the magnetic field was of relatively low intensity. Thus optimum results could not be achieved. In addition, the electric field was applied at right angles to the body's natural current flow, hindering maximum efficiency of the device. The lines of magnetic force, on the other hand, ran approximately parallel to the skin surface, and thus provided no aid in penetration of the current into the deep tissues.

United States Patents disclosing only the application of electrical stimulation to the body include Brouner U.S. Pat. Nos. 3,055,372, Jonsson 3,476,117 and Hagfors 3,645,267. Stimulation by electrical current is provided by devices disclosed in Bowers et al U.S. Pat. Nos. 3,726,285; Holcomb et al 3,773,051; Mauer 3,888,261; Weiss 3,924,641; Nozhinkov et al 3,989,051; and Geerling 4,019,519. Hallgren U.S. Pat. No. 3,841,305 discloses a device for nerve stimulation by induction. Temporary relief of arthritic pain is claimed to be provided by devices disclosed in Paul, Jr. U.S. Pat. Nos. 3,881,494, and Liss et al 3,902,502. Devices for electrotherapy by tissue stimulation are disclosed in Nawracaj U.S. Pat. Nos. 3,794,022; Horn 3,918,459; and Ellis 4,019,510. Hagfors et al 3,911,930 discloses a device for electrotherapy by application of generally rectangular or square wave pulses to the body. Manning U.S. Pat. No. 3,893,462 discloses devices for inductive stimulation of tissue as well as stimulation by direct application of current.

Another prior device with which applicant is familiar involved an applicator device containing a pair of spaced electrodes and an electromagnet therebetween. The electrodes were supplied with a relatively minimal level of direct current, within the range of 50–100 microamperes and usually 20–25 microamperes, and a voltage up to 6 volts dc. The current was reversed rapidly in polarity in an attempt to minimize adverse effect on tissue and bone structure. The electromagnet was electrically powered from a rotating potentiometer which supplied approximately 0 to 45 volts dc to the electromagnet to obtain a sweeping effect of the current into the tissue. It was subsequently determined that such device was not satisfactory because of the voltage and current parameters and because of the substantially adverse effect of the use of current reversal which apparently prevented proper tissue stimulation.

SUMMARY OF THE INVENTION

According to the present invention, there is provided a method and device which is believed to be a significant improvement over the aforementioned devices, and which achieves deep penetration of electrical current into the body tissue when desired. The device includes a first electrode from which current is emitted, an electromagnet concentrically located around the first electrode for controlling the depth of current penetration, and a second or return electrode to which the current flows through the tissues under treatment. The electrodes are placed against the patient's skin, the first electrode from which the current is emitted being located further from the brain than the second electrode to which the current flows. The magnetic lines of force from the electromagnet penetrate the body at approximately right angles. Polarities are chosen such that the magnetic field created by the electromagnet repels the current emitted by the first electrode which it surrounds, forcing the current into the body tissue to a depth determined by the strength of the magnetic field.

The current pulses are of a single, positive polarity, and are typically rectangular or square-wave pulses, but electrolysis at the tissue-electrode interface is minimized because of the spreading effect of the magnetic field on the current path. The current flows in the direction of normal nerve signals to the brain, thus emulating as nearly as possible the body's normal functions. The pulse width and rise and fall times are selected to provide therapeutic benefit to the tissue under treatment. Applicant believes this therapeutic benefit may be explained by the relationship between the selected pulse parameters and the cycle time of the sodium-potassium pump.

It is an object to the present invention, therefore, to provide an improved method and device for the therapeutic treatment of living tissue.

It is a further object of the present invention to provide an improved method and apparatus for the therapeutic treatment of tissue utilizing electric and magnetic fields in conjunction.

It is another object of the present invention to provide for deep penetration of therapeutic electrical activity into body tissues.

A still further object of the present invention is to minimize electrolysis of tissue during the application of electrical signals to the tissue.

These and other objects and advantages of the present invention will become apparent from the following detailed description taken in conjunction with the accompanying drawings.

DESCRIPTION OF THE DRAWINGS

FIGS. 1a and 1b illustrate, respectively, a cross-sectional side view and a bottom view of an electrode provided with a concentric electromagnet according to the present invention;

FIGS. 2a and 2b are block diagrams of circuits which may be used to generate, respectively, the electric and magnetic fields of the present invention;

FIGS. 3a and 3b are schematic circuit diagrams of the components of FIGS. 2a and 2b;

FIGS. 4a, 4b and 4c illustrate placement of a device according to the present invention at various locations on the body of a patient under treatment.

FIG. 5 illustrates a combined waveform that may be applied to the electromagnet of the present invention.

DESCRIPTION OF THE PREFERRED EMBODIMENT

Figure 3C:
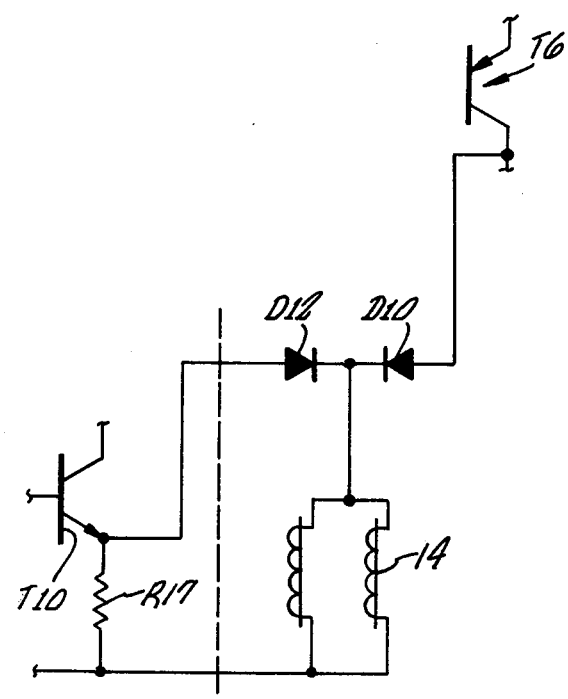
FIG. 3c is a portion of the schematic circuit diagram of FIG. 3b illustrating an alternative embodiment of the present invention.

Referring now to FIGS. 1a and 1b, there is illustrated a device 10 according to the present invention comprising a first electrode 12 and an electromagnet 14. Current to the electrode 12 is supplied through a conductor 16 which is surrounded by electrically insulating material 18 of a suitable nature. A ferrite core 20 concentrically surrounds the insulating material 18 and the conductor 16 to provide a concentrated electromagnetic field. The electromagnet 14 is wound around the ferrite core, and may comprise for example 4460 windings of #25 copper wire. The electromagnet 14 may be encased within a shell of suitable material, which may measure for example 2 inches in height, 2.25 inches in outer diameter, and 0.625 inches in inner diameter. When applied to a patient, the device 10 is positioned such that the electrode 12 is in contact with the patient's skin. A current applicator pad 13 surrounds electrode 12. The electromagnet 14 is connected to a power source which will hereinafter be described in greater detail through suitable connecting means, not illustrated, with the polarity of the current flowing through the electromagnet 14 being chosen such that the lines of the magnetic force penetrate into the patient's skin to repel the electrons emitted from the electrode 12 and force the current into the tissue.

FIG. 2a shows a block diagram of a circuit 22 for supplying current pulses to the electrode 12, comprising two timer/oscillators 24 and 26, a voltage multiplier 28, and a gating circuit 30. The output of the timer/oscillator 24 is fed through the voltage multiplier 28 and thence to the gating circuit 30, which responds to the signals provided by the voltage multiplier 28 and the timer/oscillator 26 to provide a positive rectangular or square wave current pulse to the electrode 12 via the output terminal 31a and the conductor 16 shown in FIG. 1a. The timer/oscillator 24 and voltage multiplier 28 determine the voltage of the output pulse, and the timer/oscillator 26 controls the pulse frequency and width. The second electrode utilized in the device of the present invention is not shown in detail, but may comprise any biological electrode of a type well known in the art. The second electrode is connected through suitable connecting means to the terminal 31b and thence to ground.

FIG. 2b shows a block diagram of a circuit 32 for supplying power to electromagnet 14. The circuit 32 may provide two types of electrical output, between which the operator may choose, in accordance with the nature of the treatment desired, by means of switch 34. One type of output is a positive series of pulses similar to that provided by the circuit 22 to the electrode 12, and is supplied by a circuit comprising two timer/oscillators 36 and 38, a voltage multiplier 40, and a gating circuit 42. The output of the gating circuit 42 may be selectively applied through the input 34a of the switch 34 to an output terminal 35a. Another type of electrical output is provided by a ramp voltage generator 44, which produces a sawtooth waveform output. This ramp voltage likewise may be selectively applied through the input 34b of the switch 34 to the terminal 35a. A second connection to the electromagnet 14 is made to a suitable ground via a terminal 35b.

FIGS. 3a and 3b show schematic diagrams of the circuits illustrated in block form in FIGS. 2a and 2b. A suitable power source, not shown, applies a DC voltage of, for example, nine volts at the points marked "+V".

More particularly, FIG. 3a illustrates the circuit components of the circuit 22 shown in FIG. 2. A timer/oscillator 24 provides a series of pulses whose frequency is determined by a feedback resistor R1 and a variable resistor VR1, the latter being connected in parallel with a diode D1 across the two input terminals of a timer 24a. The right-hand terminal of the resistor R1 is connected to the voltage supply +V. A capacitor C1 is similarly connected between one of the timer inputs and ground. All timers may be of a type NE 555 or other suitable device.

The output of the timer 24a is connected to the input thereof at the junction of the capacitor C1 and the variable resistor VR1, and also is provided to the base of an NPN transistor T1 through a resistor R2. The transistor T1, together with a diode D2, an inductor I1, and a capacitor C2, functions as the voltage multiplier 28 of FIG. 2a. The anode of the diode D2 and one terminal of the inductor I1 are connected to the collector of the transistor T1, the emitter of the transistor T1 being connected to the ground. The remaining terminal of the inductor I1 is connected to the voltage supply +V. The cathode of the diode D2 is connected to the capacitor C2, whose remote terminal is grounded.

The timer/oscillator 24 switches the transistor T1 on and off, causing current to flow alternately through the inductor I1. The inductor I1 causes a voltage step-up of approximately three times the supply voltage +V (for example, from 9 volts dc to 27 volts dc), which resulting voltage is stored by the capacitor C2 until discharged into the gating circuit 30 of FIG. 2a.

The timer/oscillator 26, which includes a timer 26a, is similarly provided with biasing components including a resistor R3, a variable resistor VR2, a diode D3, and a capacitor C3, for adjusting its output frequency in a manner analogous to that described in the case of the timer/oscillator 24, although the exact output frequency may vary substantially. The timer/oscillator 26 establishes the pulse frequency and pulse width. The output of the timer/oscillator 26 is provided to the base of an NPN transistor T2 through a resistor R4, the emitter of the transistor T2 being grounded. The collector of the transistor T2 is connected through a resistor R5 to the base of a PNP gating transistor T3, whose emitter is controlled by the cathode of the diode D2. The voltage stored by the capacitor C2 is gated through the transistor T3 under control of the transistor T2. The collector of the transistor T3 provides an output to the potentiometer VR3, which provides an adjustable output to the conductor 16 of the electrode 12 shown in FIG. 1. The remaining terminal of the potentiometer VR3 is grounded. Thus, the transistor T3 and the potentiometer VR3 function as the gating circuit 30 of FIG. 2a, supplying to the output terminal 31a a series of positive output pulses of selectable amplitude, width and frequency, the output voltage being determined by the voltage multiplying circuit including the transistor T1 and the pulse width and pulse frequency being determined by the timer/oscillator 26.

Referring now to FIG. 3b and circuit 32, two subcircuits are illustrated whose outputs are provided to the switch 34 for selective application to the electromagnet 14. A first output comprising positive square wave pulses is provided by the circuit in the upper right hand corner of FIG. 3b whose configuration is similar to that of the circuit 22. The timer/oscillator 36, including a timer 36a and biasing components including a resistor R6, a variable resistor VR4 connected in parallel with a diode D4, and a capacitor C4, provides an output through a resistor R7 to the voltage multiplier 40 including an NPN transistor T4, an inductor I2, a diode D5, and a capacitor C5. The timer/oscillator 38 is similarly provided with a timer 38a and biasing components including a resitor R8, a variable resistor VR5, a diode D6, and a capacitor C6, and supplies its output through a resistor R9 to the base of an NPN transistor T5, whose emitter is grounded and whose collector is connected through a resistor R10 to the base of a PNP gating transistor T6. The input to the emitter of the gating transistor T6 is provided through the cathode of the diode D5, and the collector of the gating transistor T6 supplies a fixed voltage positive square wave pulse to one of the inputs 34a of the switch 34.

A high voltage pulse (for example, 50 volts dc) is generated and controlled by the above-described portion of the circuit 32 in a manner essentially identical to that described previously in connection with the circuit 22, differing only in circuit constants and in the voltage output of the flyback inductor I2. The gating transistor T6 allows the capacitor C5 to discharge completely through the coils of the electromagnet 14. The discharge rate is limited only by the resistance and the reactive impedance of the electromagnet 14.

Turning to the portion of the circuit 32 shown at the bottom of FIG. 3b, a sawtooth waveform voltage is provided to the other input terminal 34b of the switch 34 by a ramp voltage generator 44. A voltage +V is applied to a self-starting oscillator comprising a MOS-FET Q1, a capacitor C7, and resistors R13, R14, and R15. The oscillator output is controlled by a variable resistor VR8 and is applied through a capacitor C8 to a forming stage including NPN transistors T7 and T8. Variable resistors VR6 and VR7 connected between the power supply +V and the collectors of the transistors T7 and T8 respective control the shape of the resulting waveform. The emitters of the transistors T7 and T8 are connected to ground. The collector of the transistor T8 is connected to the base of an NPN transistor T9 which, together with an NPN transistor T10 whose base is driven by the emitter of the transistor T9, forms a current amplifier. The emitter of the transistor T10 supplies a sawtooth voltage waveform varying from 0 to +V volts dc, to the terminal 34b of the switch 34 for selective application to the electromagnet 14.

FIGS. 4a, 4b and 4c illustrate typical positions of the electrodes of the present invention in use, depending on the area to be treated. The light-colored circle A represents the device 10 including the electrode 12 from which the current is emitted, and the dark-colored circle B represents a grounded electrode to which the current flows. The device 10 is always positioned further from the brain than the grounded electrode to ensure that the applied pulses are of the same polarity as normal neuronal pulses, so that the device simulates as nearly as possible the action of normal nerve signals. However, the grounded electrode B should not be placed in the area of the brain nor should the electrodes bracket the heart area, as clinical guidelines for such use have not yet been established.

By means of the circuit 22 a square-wave pulse of, for example, approximately 20 to 27 volts DC and up to 400 microamps current may be applied to the patient. The pulse width may be 3 to 6 milliseconds, but preferably should not exceed three milliseconds in order to provide maximum tissue therapy. A frequency of approximately 5 to 80 hertz may be utilized, with the best results apparently achieved at a frequency of approximately 20 to 25 hertz. Continuous treatment not to exceed six to eight hours, or 12 to 14 hours within a 24 hour period, is recommended.

The selectability between different inputs to the electromagnet affords flexibility in treatment. The normal ramp voltage from the generator 44 has a peak approximately equal to the supply voltage +V, which may be for example 9 volts, and may have a frequency of approximately 2 hertz. The pulsed output, however, may be for example 50 volts dc (peak), with a pulse width corresponding approximately to that of the current pulses supplied by the electrode to the patient (3 to 6 ms) and a frequency of 10 hertz. In this mode of operation greater current dispersion is thought to be achieved and maximum deep tissue therapy may be realized.

A wider area of treatment may also be achieved by the use of additional electromagnets connected in parallel with the first electromagnet assembly. The additional electromagnets are structured like that shown in FIG. 1, but without the electrode 12 and the conductor 16. Connected in a straight line between the positive and negative electrodes, these additional electromagnets can help maintain the flow of the current through the deep tissues. Also, the voltage generator and the pulse generator outputs can be ganged together, through a circuit which replaces the switch 34 with appropriate electrical isolation means such as diodes, to achieve a magnetic field produced by a very short pulse superimposed on the ramp voltage similar to the waveform 100 of FIG. 5. This can be accomplished by removing the switch 34, connecting the anode of a first diode D10 (FIG. 3c) to the collector of the transistor T6 and the anode of a second diode D12 to the emitter of the transistor T10, and connecting the cathodes of both diodes directly to the electromagnet 14 at the point marked 35a in FIG. 2b. In addition, a plurality of assemblies such as the device 10 of FIG. 1 may be utilized simultaneously in conjunction with a single return electrode such as electrode B of FIGS. 4a, 4b and 4c, to provide treatment of several areas of the body, as long as the guidelines for placement of the electrodes A and B and observed (that is, electrode B being closer to the brain than each electrode A).

The device of the present invention may be totally powered by a rechargeable battery, to prevent any possibility of harmful shocks being inadvertently applied to the patient.

Exemplary values of the circuit constants employed herein are provided for illustrative purposes only in Table 1.

TABLE 1

| | |
|---|---|
| R1 | 4.7Ω |
| R2 | 1KΩ |
| R3 | 15 KΩ |
| R4 | 4.7 KΩ |
| R5 | 56KΩ |
| R6 | 4.7KΩ |
| R7 | 1KΩ |
| R8 | 10KΩ |
| R9 | 1.2KΩ |
| R10 | 470Ω |
| R11 | 11KΩ |
| F12 | 1MΩ |
| R13 | 1KΩ |
| R14 | 150KΩ |
| R15 | 56Ω |
| R16 | 1MΩ |
| R17 | 11KΩ |
| C1 | 0.0022 μf |
| C2 | 20 μf |
| C3 | 0.1 μf |
| C4 | 0.0022 μf |
| C5 | 100 μf |
| C6 | 10 μf |
| C7 | 5 μf |
| C8 | 5 μf |
| All diodes | IN 914 |
| VR1 | 0–5KΩ |
| VR2 | 0–2MΩ |
| VR3 | 0–10KΩ |
| VR4 | 0–5KΩ |
| VR5 | 0–250KΩ |
| VR6 | 0–10KΩ |
| VR7 | 0–10KΩ |
| VR8 | 0–250KΩ |
| I1 | 100 MHY |
| I2 | 150 MHY |
| T1, T2, T4, T5, T7, T8, T9 | 2N 2222A |
| T3 | 2N 2906A |
| T6 | HEP 242 |
| T10 | HEP 241 |
| Q1 | 2N 2646 |

While a preferred embodiment of the present invention has been described, it is to be understood that numerous modifications thereof will be apparent to those skilled in the art without departing from the spirit of the present invention, and the same are intended to be embraced within the appended claims.

I claim:

1. A method for the therapeutic treatment of living tissue comprising the steps of
    generating a series of rectangular, positive electrical pulses of predetermined amplitude, frequency, and duration,
    generating a magnetic field,
    positioning a first electrode and a second electrode against the tissue to be stimulated,
    applying said electrical pulses to said tissue through said first electrode,
    applying said magnetic field in the area of said first electrode and substantially at right angles to the surface of said tissue to aid the penetration of said electrical pulses into said tissue, and
    providing an electrical return path from said tissue through said second electrode.

2. The method of claim 1 wherein the step of generating said magnetic field includes the steps of generating a second series of positive rectangular electrical pulses of adjustable amplitude, frequency, and duration and applying said second series of pulses to an electromagnet.

3. The method of claim 1 wherein the step of generating said magnetic field includes the step of generating a continuously varying voltage and applying said continuously varying voltage to an electromagnet.

4. The method of claim 3 wherein said continuously varying voltage comprises a sawtooth waveform.

5. The method of claim 1 wherein the step of generating a series of rectangular, positive electrical pulses includes varying the amplitude, frequency, and duration of said electrical pulses.

6. The method of claim 5 wherein said electrical pulses have a frequency in the range of approximately 5 to 80 hertz and a duration in the range of approximately 3 to 6 milliseconds.

7. The method of claim 6 wherein the step of generating a magnetic field includes generating a second series of positive rectangular, pulses of adjustable amplitude, frequency and duration and applying the second series of pulses to an electromagnet.

8. The method of claim 7 wherein said adjustable second series of pulses has a frequency in the range of approximately 5 to 80 hertz and a duration in the range of approximately 3 to 6 milliseconds.

9. The method of claim 1 wherein the step of positioning said first electrode and said second electrode includes positioning said first electrode with respect to said second electrode to cause current to flow between said electrodes in a predetermined direction.

10. The method of claim 9 wherein said step of positioning said first electrode and said second electrode includes the additional step of positioning said first electrode father from the brain than said second electrode.

11. The method of claim 1 wherein the step of applying said magnetic field includes positioning said magnetic field substantially concentrically around said first electrode.

12. A method for the therapeutic treatment of living tissue comprising the steps of
    generating a series of rectangular, positive electrical pulses of adjustable amplitude, frequency, and duration, generating a magnetic field, positioning a first electrode and a second electrode against the tissue to be stimulated such that the current flows between said electrodes in the same direction as ordinary nerve signals in said living tissue, applying said electrical pulses to said tissue through said first electrode, applying said magnetic field substantially at right angles to the surface of said tissue and substantially concentrically around said first electrode to aid the penetration of said electrical pulses into said tissue, and providing an electrical return path from said tissue through said second electrode.

13. Apparatus for the therapeutic treatment of living tissue, comprising means for applying positive, rectangular electrical current pulses to said tissue, and means for applying a magnetic field in the area of said current pulses and at substantially right angles to the surface of said tissue to aid the penetration of said electrical pulses into said tissue.

14. The apparatus of claim 13 wherein said apparatus additionally comprises means for adjusting the amplitude, frequency, and duration of said electrical pulses.

15. The apparatus of claim 13 wherein said means for applying a magnetic field comprises an electromagnet supplied with positive rectangular electrical impulses.

16. The apparatus of claim 13 wherein said means for applying a magnetic field comprises an electromagnet supplied with a continuously varying voltage.

17. The apparatus of claim 13 wherein said means for applying a magnetic field comprises an electromagnet supplied with both positive rectangular electrical pulses and a continuously varying voltage simultaneously.

18. The apparatus of claim 13 wherein said means for applying said current pulses comprises an emitting electrode adopted to be positioned against said living tissue and said means for applying a magnetic field comprises an electromagnet.

19. The apparatus of claim 18 wherein said electromagnet is disposed concentrically around said emitting electrode.

20. The apparatus of claim 13 further including a return electrode adapted to be positioned against said living tissue.

21. The apparatus of claim 20 wherein said return electrode is located closer to the brain than said emitting electrode.

22. Apparatus for the therapeutic treatment of living tissue, comprising a first electrode adapted to be positioned against said living tissue, an emitting electrode adapted to apply positive, rectangular electrical current pulses to said living tissue, an electromagnet for applying a magnetic field substantially at right angles to said living tissue in the area of said emitting electrode to aid the penetration of said electrical pulses into said tissue, and means for generating said electrical current pulses and said magnetic field.

23. The apparatus of claim 22 wherein said apparatus additionally comprises means for adjusting the amplitude, frequency, and duration of said electrical pulses.

24. The apparatus of claim 19 wherein said electrical pulses have a frequency in the range of approximately 5 to 80 hertz and a duration in the range of approximately 3 to 6 milliseconds.

25. The apparatus of claim 22 wherein said first electrode and said emitting electrode are adapted to be positioned against said living tissue to cause current to flow between said electrodes in a predetermined direction.

26. The apparatus of claim 25 wherein said return electrode is located closer to the brain than said emitting electrode.

27. The apparatus of claim 22 wherein said electromagnet is disposed concentrically around said emitting electrode.

* * * * *